United States Patent [19]

Löfås et al.

[11] Patent Number: 5,716,854
[45] Date of Patent: Feb. 10, 1998

[54] SOLID PHASE BINDING ASSAY

[75] Inventors: Stefan Löfås; Inger Rönnberg; Katarina Lagerström, all of Uppsala, Sweden

[73] Assignee: Pharmacia Biosensor AB, Uppsala, Sweden

[21] Appl. No.: 30,169

[22] PCT Filed: Sep. 26, 1991

[86] PCT No.: PCT/SE91/00649

§ 371 Date: Apr. 1, 1993

§ 102(e) Date: Apr. 1, 1993

[87] PCT Pub. No.: WO92/06380

PCT Pub. Date: Apr. 16, 1992

[30] Foreign Application Priority Data

Oct. 1, 1990 [SE] Sweden .................... 9003122

[51] Int. Cl.⁶ .................................. G01N 33/543
[52] U.S. Cl. .................. 436/518; 436/501; 436/524; 436/532; 435/7.92; 435/7.93; 435/7.94; 435/7.95
[58] Field of Search ...................... 436/578, 501, 436/524, 532; 435/7.92, 7.93, 7.94, 7.95

[56] References Cited

U.S. PATENT DOCUMENTS

| | | | |
|---|---|---|---|
| 4,287,300 | 9/1981 | Gibbons et al. | 435/5 |
| 4,829,009 | 5/1989 | Graves | 436/578 |
| 5,244,630 | 9/1993 | Khalil et al. | 422/52 |
| 5,459,078 | 10/1995 | Kline et al. | |
| 5,459,080 | 10/1995 | Adamczyk et al. | |

FOREIGN PATENT DOCUMENTS

| | | |
|---|---|---|
| 0230768 | 8/1987 | European Pat. Off. |
| 0406473 | 7/1989 | European Pat. Off. |
| 0406473 | 1/1991 | European Pat. Off. |
| 8302954 | 9/1983 | WIPO |
| 9005303 | 5/1990 | WIPO |
| 9005305 | 5/1990 | WIPO |

OTHER PUBLICATIONS

Graves, Howard C.B., Journal of Immunological Methods, 111 (1988) pp. 157–166.

*Primary Examiner*—Christopher L. Chin
*Assistant Examiner*—Bao-Thuy L. Nguyen
*Attorney, Agent, or Firm*—Birch, Stewart, Kolasch & Birch, LLP

[57] ABSTRACT

An assay method comprising the step of binding a second substance to a first substance immobilized to a solid phase surface, the first substance being either a ligand or a species bound directly or indirectly thereto. The method is characterized in that the solid phase surface having the first substance immobilized thereto exhibits and electric charge, and that the reaction for binding the second substance to the first substance is performed at an ionic strength below 100 mM, and at such pH conditions that the electric charge of the second substance is opposite to that of the solid phase surface so that the second substance is electrostatically attracted by the solid phase surface to be concentrated thereto.

40 Claims, 5 Drawing Sheets

SOLID PHASE BINDING ASSAY

The present invention relates to an improvement in assay methods comprising the specific binding of a second substance to a first substance already bound to a solid phase surface.

In our WO 90/05303 there are disclosed sensing surfaces capable of selective biomolecular interactions and designed to be used in biosensor systems, particularly systems based upon surface plasmon resonance (SPR). In this type of optical biosensors changes in the refractive index in a layer close to a thin metal film are detected by the consequential changes of the intensity of a totally reflected light beam. For a more detailed description of such a biosensor, see our WO 90/05295 relating to an optical biosensor system, and our WO 90/05305 relating to a sensor unit and its use in biosensor systems.

The above mentioned sensing surfaces comprise a film of a free electron metal, preferably silver or gold, having one of its faces coated with a densely packed monolayer of specific organic molecules. To this monolayer a biocompatible porous matrix, e.g., a hydrogel, is bound, which matrix is employed for immobilizing a suitable ligand for a target biomolecule to be determined by the particular biosensor.

To make the matrix bind a desired ligand it is activated by the introduction of suitable functional groups, the matrix thereby normally obtaining a positive or negative net charge. Provided that the ligand to be bound, typically a protein, is of the opposite charge, the electrostatic interaction between the ligand and the matrix will concentrate the ligand at the surface and thereby provide for efficient binding of the ligand to the surface. Such binding to electrically charged surfaces has been well-known in the art for a long time, such as in enzyme immobilization and affinity chromatography (see, e.g., U.S. Pat. No. 4,829,009, WO 83/02954, and J. Immunol. Methods 1988, vol. 111(2), p. 157–66).

Although such an electrostatic effect is advantageous for the binding of ligands, the possible presence of a residual charge at the solid surface after the ligand binding has, however, hitherto been believed to be a possible source of problems in the subsequent analytical steps because of undesired ionic interactions with the sample.

It has now, in accordance with the present invention, surprisingly been found that the provision of a residual charge at the solid surface remaining after the binding of a ligand thereto may be favourably utilized to facilitate and optimize the binding of an analytical species in the subsequent steps of a particular assay to be performed at the solid phase surface. In the present context the term "analytical species" means any reactive species used in the assay except the initially bound ligand. Thus, for example, in a sandwich type assay, the so-called secondary antibody (in SPR-assay serving as an "enhancement agent") may be efficiently concentrated to the matrix by the created electrostatic interaction resulting in a substantially complete binding to the primary analyte already bound to the ligand, provided that, on one hand, the matrix has an original charge sufficient to leave a residual charge after the immobilization of the ligand thereto, and, on the other hand, that the reaction conditions are selected properly in terms of ionic strength and pH.

Thus, for the purposes of the present invention the reaction conditions involve low ionic strength and an appropriate pH of the reaction medium to ensure a negative or positive charge of the secondary antibody opposite to the charge of the solid phase surface, in contrast to the physiological conditions used in the prior art, i.e., medium ionic strength and about neutral pH. For instance, in the case of a residual negative charge of the matrix, the pH should be selected below the isoelectric point of the antibody to make the latter positively charged, and vice versa. Under these conditions the electrostatic interactions between such opposite charges of the matrix and the secondary antibody will be utilized without too many screening ions being present. It is also believed that under such conditions the matrix per se will be more open due to internal repelling in the polymer layer, thereby providing for an increased availability of the bound analyte.

To ensure that only the desired specifically active substance is bound to the surface, the importance of which of course depends on the particular application, it may subsequently to the binding step, promoted by the electrostatically caused concentration of secondary reagent in accordance with the invention, be necessary to subject the surface to moderate or high ionic strength conditions to remove species which have only bound electrostatically.

The improvements resulting from performing an assay as above in accordance with the present invention in contrast to normal conditions will reside in (i) higher sensitivity and larger dynamic range of the assay, (ii) considerably reduced consumption of secondary antibody, and (iii) faster analyses.

It will be appreciated that the electrostatic interaction derived concentrating effect described above may be utilized not only in other types of SPR-assays than sandwich assays, as will be further explained below, but also more generally in analytical methods on the whole, such as, e.g., per se conventional ELISA type analyses, as long as they involve the use of a solid phase modified or capable of being modified by a charged matrix of suitable type.

In its broadest aspect the present invention thus relates to an assay method comprising the step of binding a second substance to a first substance immobilized to a solid phase surface, the first substance being either a ligand or a species bound directly or indirectly thereto, such as an analyte or a secondary reagent bound to the analyte, the method being characterised in that the solid phase surface which has the first substance immobilized thereto exhibits an electric charge, and that the reaction for binding the second substance to the first substance is performed at an ionic strength below 100 mM, and at such pH conditions that the electric charge of said second substance is opposite to that of the solid phase surface so that the second substance is electrostatically attracted by the solid phase surface.

As mentioned above the method may include the step of subjecting the surface to higher ionic strength conditions after the binding of the second substance in order to remove unspecific binding.

It is to be noted that although the invention basically is intended to be applicable to all steps in an assay subsequent to the immobilization of the ligand, the second substance, especially in immunological assay contexts, is mostly not the analyte to be determined in the assay, since the sample to be tested does not usually comply with the required conditions as to ionic strength and/or pH and it is usually not desired to disturb the sample environment, e.g., for a serum sample. In certain cases, however, the electrostatic concentrating effect of the invention may be utilized also for the binding of the analyte depending on the particular sample.

Thus, in one embodiment of the present invention the second substance is the secondary component in a sandwich type assay, as already discussed above.

In another embodiment the second substance is an agent used for blocking residual binding sites after the immobilization of the ligand to the surface, which sites would otherwise disturb a particular analytical procedure.

In still another embodiment the second substance is an analyte, the method of the invention, e.g., being used to determine the amount of activity (ligands) immobilized to a surface.

Basically, however, the second substance may be any analytical substance for which the specified reaction conditions may be conveniently applied without any negative practical implications.

The second substance is typically a protein or polypeptide or active fragment thereof, but may generally be any substance susceptible to binding in a desired solid phase assay. As will readily be understood, said second substance is primarily a larger type molecule, e.g., a macromolecule, the diffusion rate being higher for smaller molecules and the effect achieved by the present invention thereby being of less significance.

As is readily appreciated by the person skilled in the art the above mentioned first substance may, especially as an analyte, be for example a protein or polypeptide, such as an antigen or antibody, protein A or G, an enzyme, a lectin, avidin, etc; or a hapten, hormone, sugar, biotin, toxin, vitamin, etc.

The above mentioned proteins and polypeptides, and fragments thereof, of course include both natural and synthetic or semisynthetic substances, such as proteins and polypeptides modified by chemical means or by genetic engineering techniques. An example is chimeric, i.e., bi- or polyfunctional molecules, such as bi- or polyfunctional antibodies. For the application of such molecules in biosensor surface contexts see our aforementioned WO 90/05305. Also, in e.g., a sandwich type assay, the secondary reagent may be a bifunctional antibody or other molecule to permit subsequent reaction with a tertiary reagent.

The solid phase surface layer referred to above will depend on the type of analytical method to be used. For biosensor applications, e.g., SPR or electrochemical biosensors, this layer may be a polymer layer, preferably a hydrogel, such as a dextran layer, bound to a metal surface. For the binding of a ligand thereto, the polymer layer is provided with suitable functional groups, and as a result thereof the surface layer may obtain a residual positive or negative electric charge sufficient for the purposes of the invention, but such electric charge may also be introduced in a separate treatment of the surface layer. Examples of surfaces for biosensor applications are given in our WO 90/05303 referred to above and the disclosure of which is incorporated by reference herein.

As will appear from the above "low ionic strength" is in the context of the present invention defined as being below 100 mM, the "normal" ionic strength in the typical immunological methods being about 150 mM. Preferably, however, the ionic strength is lower than 50 mM and more preferably below 20 mM. Although the ionic strength in the theoretically ideal situation should be at least near zero, this would not be possible in most practical cases, due e.g., to stability considerations for proteins, etc.

The necessary pH value to ensure a suitable charge of the second substance will, of course, vary with the nature of the particular substance. For example, in the case of a protein the pH to be selected will depend on the isoelectric point ($I_p$) of the protein, a positive charge being obtained at pH values above $I_p$ and a negative charge being obtained at pH values below $I_p$. For a particular protein having a specific $I_p$, the pH to be selected should generally differ from the $I_p$ by at least 0.5 in the desired direction. Some protein samples, such as polyclonal antibody mixture, may exhibit a pH range rather than a single pH value for its $I_p$, and in such a case the pH difference given above should, of course, instead relate to the relevant range limit of the pH interval, i.e. at or below 4.5 for a polyclonal mixture having a pH range from 5 to 8. In this context it is also to be noted that the $I_p$ of a specific protein may be modified by per se conventional methods to suit, for instance, a particular charged matrix.

The method according to the invention is particularly suitable for immunochemical type assays or analytical methods, especially biosensor related methods. As has already been discussed above, the inventive concept is thus advantageously applicable to the binding of the secondary antibody in an immunological sandwich assay, the sensitivity as well as the dynamic range of the reaction being considerably increased.

Another valuable application of the present invention, also mentioned above, is for efficient blocking of surplus binding sites. This is useful in, for example, so-called epitope mapping by biosensor technology) (see e.g. our WO 90/05306 relating to the characterization of macromolecules by means of biosensor technology) where a monoclonal antibody is first bound to a sensing surface having immobilized thereto antibodies capable of generally binding mouse antibodies (e.g. of the type rabbit anti-mouse G1 or $F_c$). The mapping is then performed by sequentially passing the analyte (antigen) and a second specific monoclonal over the surface, binding of the latter indicating that the two monoclonals bind to different sites on the antigen. As is readily understood the amount of the generally binding antibody immobilized to the surface must be relatively high to permit binding of a sufficient amount of the first monoclonal from the relatively low concentration present in, for example, a culture medium. Since the second monoclonal must not bind to the initially immobilized generally binding antibody, which would be interpreted as a false positive response, the surplus binding sites of the generally binding antibody not occupied by the first monoclonal must be blocked by non-specific antibodies. In accordance with the present invention this may be done in a more efficient and reagent saving way if the above described electrostatic concentrating effect is utilized by providing the blocking antibody in a buffer of low ionic strength and at a pH conferring a charge to the blocking antibody that is opposite to that of the sensing surface matrix.

The same concept may be used to block surplus binding sites at a surface having protein A or G immobilized thereto to make it capable of generally binding polyclonal antibodies. In this case the electrostatic effect may, depending on the pH, be used to improve both the binding of the ligand to the protein A or G, and the subsequent blocking of residual binding sites.

Hereinafter the invention will be described by way of some specific examples, which are given only for the purpose of illustration, and which are not to be construed as limiting in any sense whatsoever. In connection herewith reference will be made to the accompanying drawings, in which:

FIG. 1 is a graph showing the surface change response when binding secondary antibody to a biosensor surface in a sandwich assay for $\beta_2$-microglobulin at high ($\Diamond$) and low ($\square$) ionic strength, respectively;

FIG. 2 is a similar graph as in FIG. 1 showing the surface change response when binding secondary antibody to a biosensor surface in a sandwich assay for luteinizing hormone (LH) at (i) a secondary antibody concentration of 1 mg/ml at high ($\square$) and low ($\Diamond$) ionic strength; (ii) a secondary antibody concentration of 250 µg/ml at low ionic strength (■); and (iii) a secondary antibody concentration of 50 µg/ml (◆) at low ionic strength;

Figure 1:
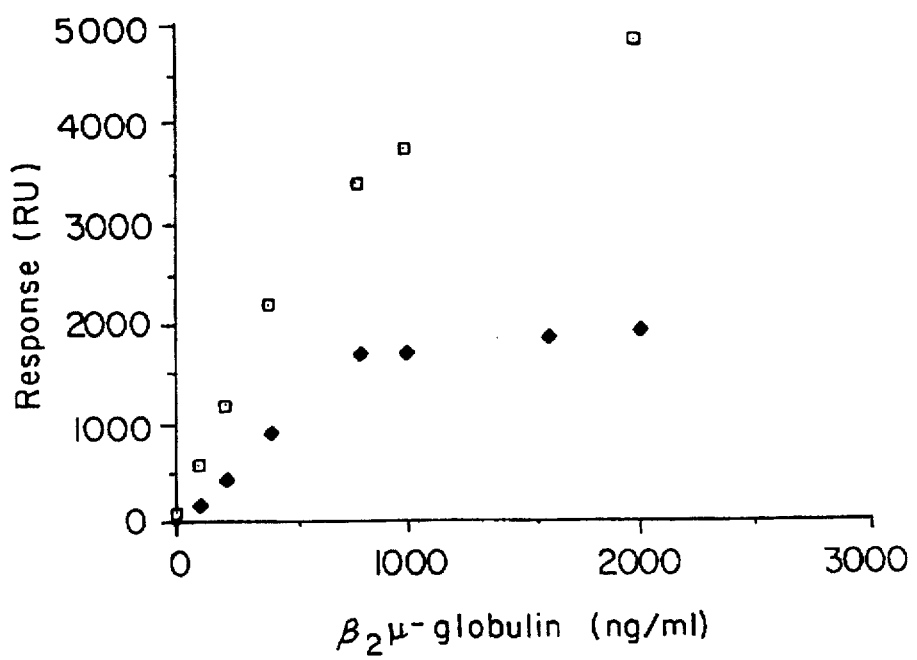

All the assays in the examples were performed with a surface plasmon resonance biosensor system of a type disclosed in our WO 90/05295 (the disclosure of which is incorporated by reference herein) and now commersialized under the trade name BIAcore by Pharmacia Biosensor AB, Uppsala, Sweden. This biosensor system comprises a replaceable sensor unit, a block unit for liquid handling having a conduit system for transporting the reagent and the sample solutions over the sensing surface of the sensor unit, an optical unit which couples incident light rays to the sensing surface and detects the reflected radiation, and an evaluation unit which after calibration transforms the detector signal into a parameter proportional to the amount of substance at the sensing surface. When performing a measurement, a defined sample liquid volume is introduced by injection into a defined conduit section, which liquid volume is then by means of eluent liquid, or drive buffer, forced to pass the sensing surface for optical analysis.

The sensor unit which the sensing surface was a Sensor Chip CM 5 (Pharmacia Biosensor AB, Uppsala, Sweden) which is a glass substrate supported gold film to which is bound a matrix constructed from a composite of a metal-protection layer (an adsorbed monoclonal of long-chain 1,ω-hydroxyalkyl thiols) and a covalently bound flexible carboxymethyl-modified dextran hydrogel having a negative charge. For the preparation of such a sensing surface see our above mentioned WO 90/05303.

The measurements were performed substantially as described in our aforementioned WO 90/05305, the disclosure of which is incorporated by reference herein. The drive buffer used throughout the examples was HBS (Hepes buffer saline), pH 7.4, as specified below. The surface change response in the measurements is expressed in "resonance units" (RU); a response of 1000 RU corresponds to a 0.1° shifts in the resonance angle (the angle of the incident light beam, relative to the sensor surface, at which surface plasmon resonance occurs) or a change of 1 ng/mm$^2$ in the surface concentration.

EXAMPLE 1

Sandwich Assay for $\beta_2$-microglobulin

A sandwich assay for $\beta_2$-microglobulin was performed by first immobilizing to the sensing surface a polyclonal monoclonal specifically directed against $\beta_2$-microglobulin. This was effected by activating the surface with 0.2M N-ethyl-N'-(3-dimethylaminopropyl)carbodiimide (EDC) and 0.05M N-hydroxysuccinimide (NHS) in distilled water, applying the antibody in coupling buffer (10 mM sodium acetate, pH 5.0) to the surface, and deactivating any excess of EDC and NHS with 1M ethanolamine, pH 8.5. In a test cycle the sensing surface was then sequentially passed by a sample containing $\beta_2$-microglobulin (analyte) and a secondary reagent in the form of a polyclonal Ig-fraction (2.5 mg/ml; 10% specific activity), respectively, and the response for the secondary reagent was measured. Each test cycle was terminated by regenerating the surface with 10 mM HCl, pH 2.2. The assay was run with different concentrations of the analyte and at low ionic strength (10 mM Hepes buffer, 0.005% Tween® 20, pH 7.5) and high ionic strength (Hepes buffer including 0.15M NaCl, pH 7.5), respectively, of the secondary reagent. The results are shown in Table 1 below and in FIG. 1 in the drawings.

TABLE 1

| $\beta_2\mu$-globulin | Response of secondary reagent | |
|---|---|---|
| ng/ml | Low i.s.* | High i.s.* |
| 0 | 72 | 173 |
| 100 | 563 | 173 |
| 200 | 1187 | 417 |
| 400 | 2190 | 900 |
| 800 | 3360 | 1888 |
| 1000 | 3738 | 1672 |
| 1600 | — | 1862 |
| 2000 | 4847 | 1912 |

*i.s. = ionic strength

As appears from the table and FIG. 1 a more than 3 times higher response for the low ionic strength is obtained for an analyte concentration of 100 ng/ml. At an analyte concentration of about 800 ng/ml the secondary response levels out at high ionic strength, whereas it still increases at 2000 ng/ml at low ionic strength. Since the runs were performed at a pH of 7.5 and the $I_p$ of the secondary antibody is about 8.5, the latter was positively charged at this pH.

EXAMPLE 2

Sandwich Assay for Luteinizing Hormone

Figure 2:
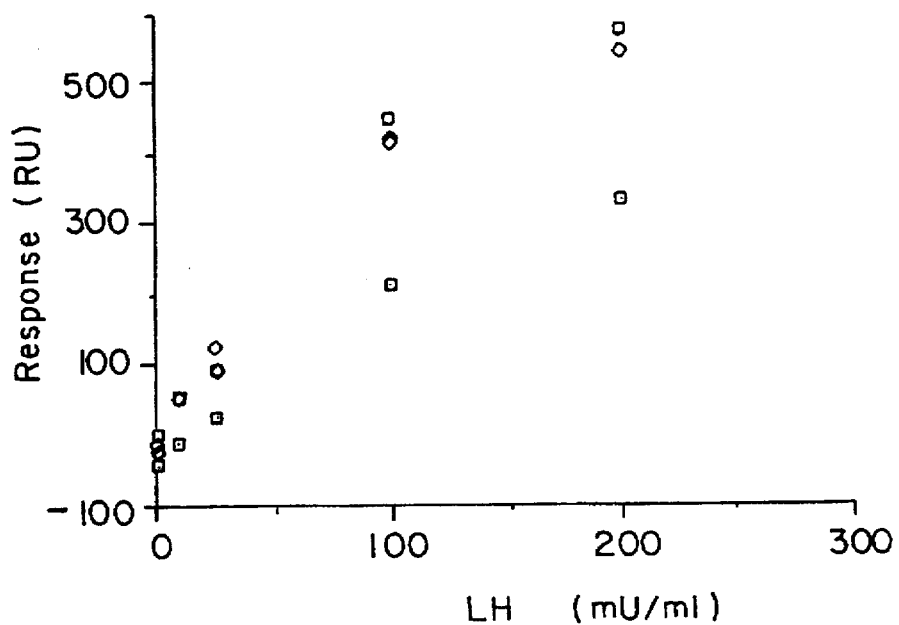

A sandwich assay for luteinizing hormone is performed in the same manner as in Example 1 by first immobilizing to the sensing surface a monoclonal antibody specifically directed against luteinizing hormone (LH), and then sequentially passing the LH containing sample (analyte) and a monoclonal anti-LH antibody as the secondary reagent, respectively, over the surface. Samples with different concentrations of the LH-analyte were analyzed by observing the response of the secondary reagent at different concentrations and high and low ionic strength, respectively (Hepes buffer with and without 0.1M NaCl). The results are shown in the following Table 2 and in FIG. 2 of the drawings.

TABLE 2

| Analyte | Response of secondary reagent * | | | |
|---|---|---|---|---|
| conc. mU/ml | 1 mg/ml High i.s. | 1 mg/ml Low i.s. | 250 µg/ml Low i.s. | 50 µg/ml Low i.s. |
| 0 | −24 | −17 | −6 | −7 |
| 0.5 | −41 | −11 | −3 | −7 |
| 2 | −36 | −1 | 3 | 1 |
| 10 | −10 | 49 | 56 | 52 |
| 25 | 26 | 121 | 91 | * |
| 100 | 213 | 422 | 447 | 411 |
| 200 | 334 | 570 | 578 | 543 |

*Negative values are caused by a slight decrease of the base line level in the course of the assay.

As appears from the table the concentration of the secondary reagent may be reduced by 20 times when buffer of low ionic strength is used in comparison with the corresponding procedure at high ionic strength. Yet both higher sensitivity and greater dynamic are obtained. The higher sensitivity is, for example, observed at the LH-analyte concentration 10 mU/ml when the secondary response is 50 RU for low ionic strength and a secondary reagent concentration of 50 µg/ml, while the same analyte concentration does not give any significant response at high ionic strength and a secondary reagent concentration of 1 mg/ml.

Figure 3:
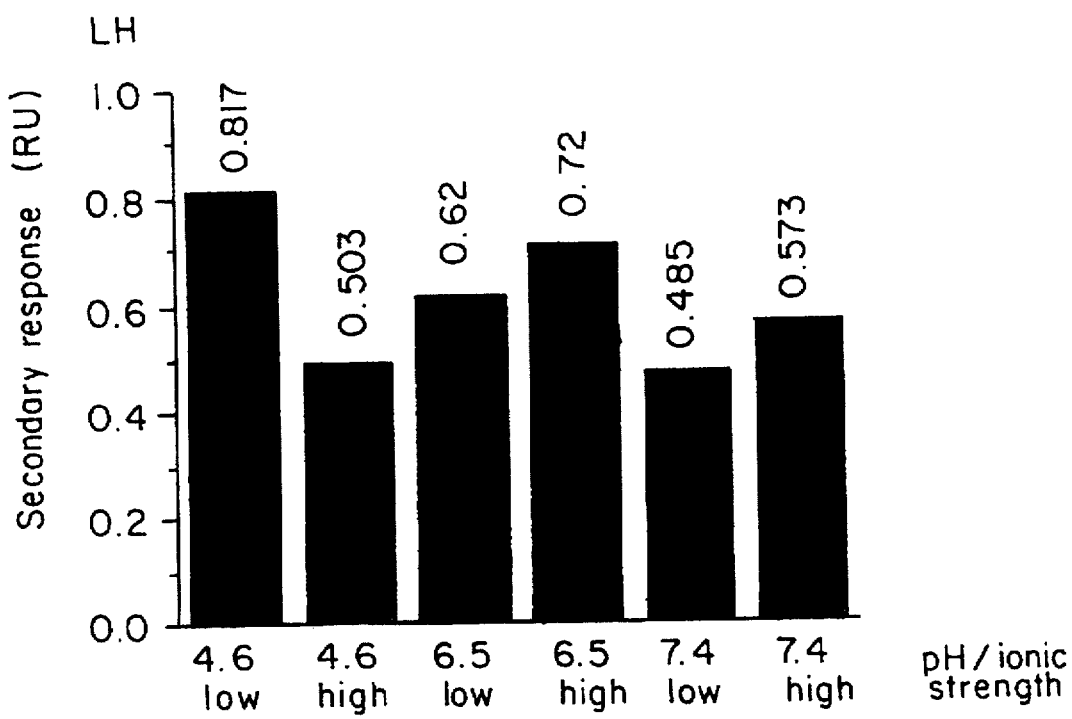
FIG. 3 is a staple diagram showing the pH dependency of the surface change response for the binding of a secondary antibody to a biosensor surface in a sandwich assay for LH at a secondary antibody concentration of 1.0 mg/ml.
Figure 4:
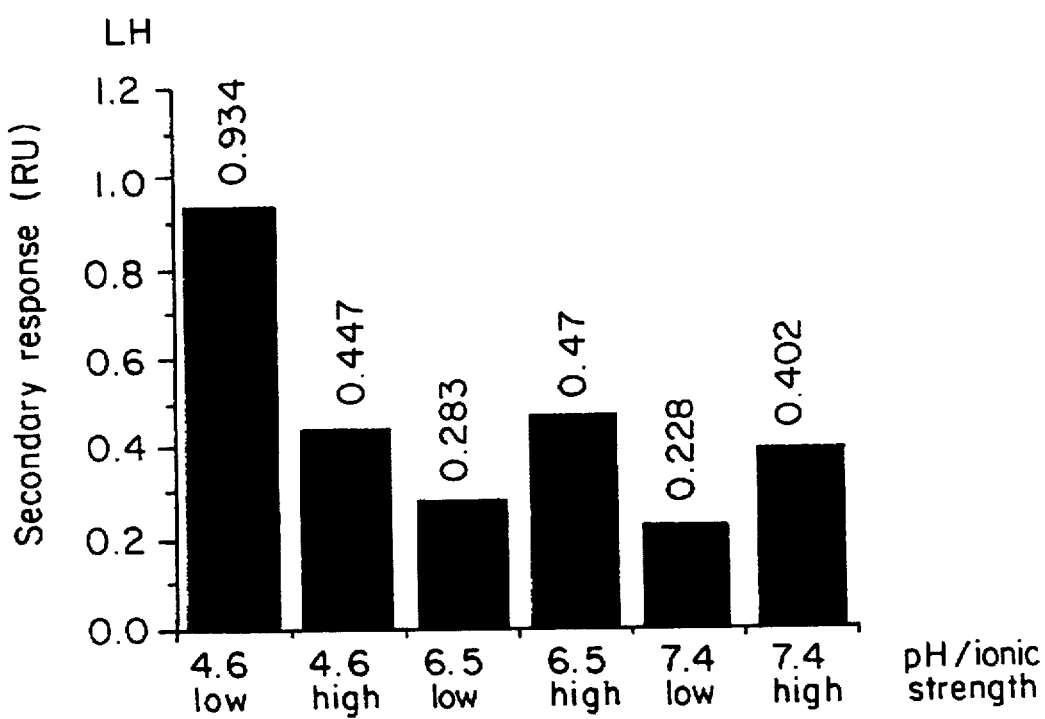
FIG. 4 is a staple diagram showing the pH dependency of the surface change response for the binding of a secondary antibody to a biosensor surface in a sandwich assay for LH at a secondary antibody concentration of 50 µg/ml.
Figure 5:
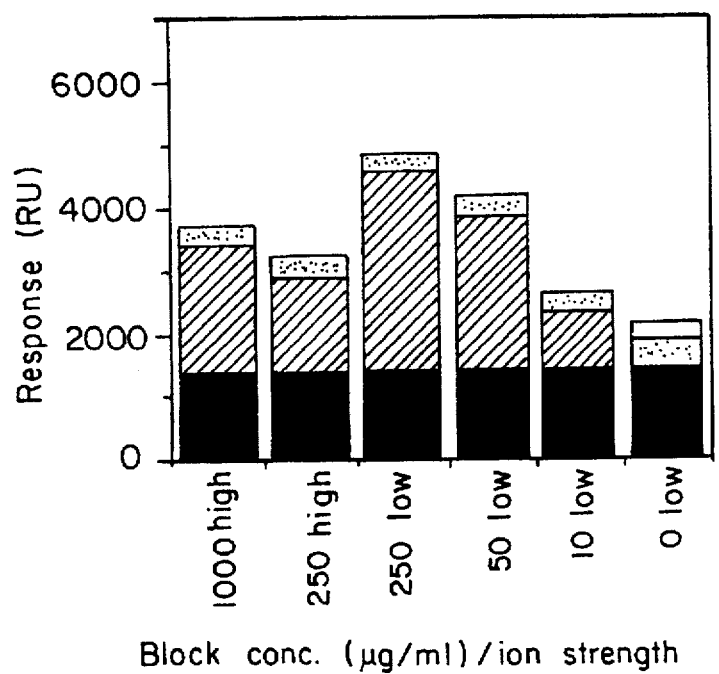
FIG. 5 is a staple diagram showing the surface change response of a biosensor surface for the sequential binding of a first LH-specific monoclonal (■); blocking antibody (□), LH ( ), and the possible subsequent binding of the original monoclonal (□) at various concentrations of blocking antibody and at high and low ionic strength, respectively.
Figure 6:
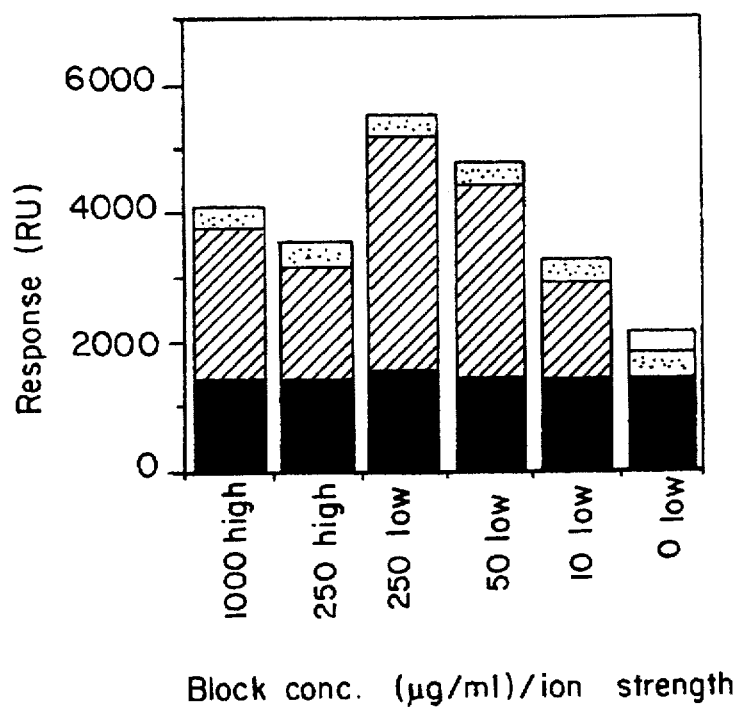
FIG. 6 is a staple diagram showing the surface change response of a biosensor surface for the sequential binding of a second LH-specific monoclonal (■); blocking antibody (□), LH ( ), and the possible subsequent binding of the original monoclonal (□) at various concentrations of blocking antibody and at high and low ionic strength, respectively.
Figure 7:
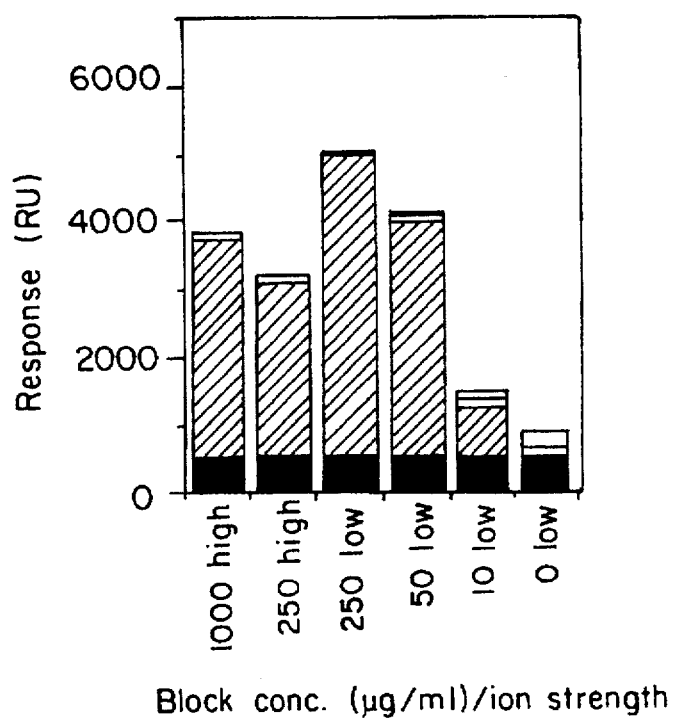
FIG. 7 is a staple diagram showing the surface change response of a biosensor surface for the sequential binding of a third LH-specific monoclonal (■); blocking antibody (□), LH ( ), and the possible subsequent binding of the original monoclonal (□) at various concentrations of blocking antibody and at high and low ionic strength, respectively.

Corresponding assay runs were performed to study the pH-dependency of the secondary response, and the results are shown in FIGS. 3 and 4; LH was used at a concentration of 1000 ng/ml and two different concentrations of secondary antibody were used, viz. 1.0 mg/ml (FIG. 3) and 50 µg/ml (FIG. 4). Similarly as in FIG. 2, at pH-values above that of the secondary antibody $I_p$ (5.3) the low ionic strength gives lower responses than those at the high ionic strength. This is due to the antibody then being repelled by the negative charge of the matrix, which effect to a certain extent may be compensated for by higher concentrations. At pH-values below the $I_p$ of the antibody the results are, however, the opposite, the low ionic strength giving a more than doubled response at an antibody concentration of 50 µg/ml.

EXAMPLE 3

Blocking of Surplus Binding Sites

Rabbit anti-mouse G1 antibody (RAMG1) (Phamacia Diagnostics AB, Uppsala, Sweden), dissolved in 10 mM sodium acetate, pH 5.0, to 30 µg/ml, was immobilized to the sensing surface in the same way as in Examples 1 and 2 above. Luteinizing hormone (LH) specific monoclonal, dissolved in HBS (Hepes buffer saline: 10 mM Hepes, 0.15M NaCl, 3.4 mM EDTA, 0.05% Tween®) was then applied to the surface, whereupon a blocking monoclonal antibody against alphafetoprotein (AFP), dissolved in Hepes-buffer (10 mM Hepes, 3.4 mM EDTA, 0.05% Tween®) with and without, respectively, NaCl (0.15M) was passed over the surface to block any residual binding sites not occupied by the LH-monoclonal. LH-analyte (International Enzymes Inc., U.S.A.) dissolved in Pharmacia Diluent (Pharmacia Diagnostics AB, Uppsala, Sweden) to 10 µg/ml was then allowed to react with the surface. To test for the presence of residual non-specific RAMG1 sites, the originally bound monoclonal was again passed over the surface, binding of the monoclonal indicating inefficient blocking.

Three different monoclonals, designated 2, 5 and 10, were used. Whereas monoclonals 2 and 5 were used in culture medium, monoclonal 10 was studied both in culture medium and purified at two different concentrations, 7 and 70 µg/ml, in HBS-buffer.

The blocking antibody was used at high ionic strength (with NaCl) at two concentrations, 1000 and 250 µg/ml, and at low ionic strength (without NaCl) at four concentrations, 0, 50, 10 and 250 µg/ml.

The results are shown in FIGS. 5–10.

As appears from the Figures, the blocking can be effected much more efficiently and reagent saving if the electrostatic concentrating effect of the invention is utilized by providing the blocking antibody in a buffer of low ionic strength and at a pH below the $I_p$ of the antibody (i.e., where it is positively charged). This may, for example, be seen from a comparison of staples 2 and 3 in FIGS. 5–9, wherein 250 µg/ml of non-specific blocking antibody at high and low, respectively, ionic strength are compared.

Figure 8:
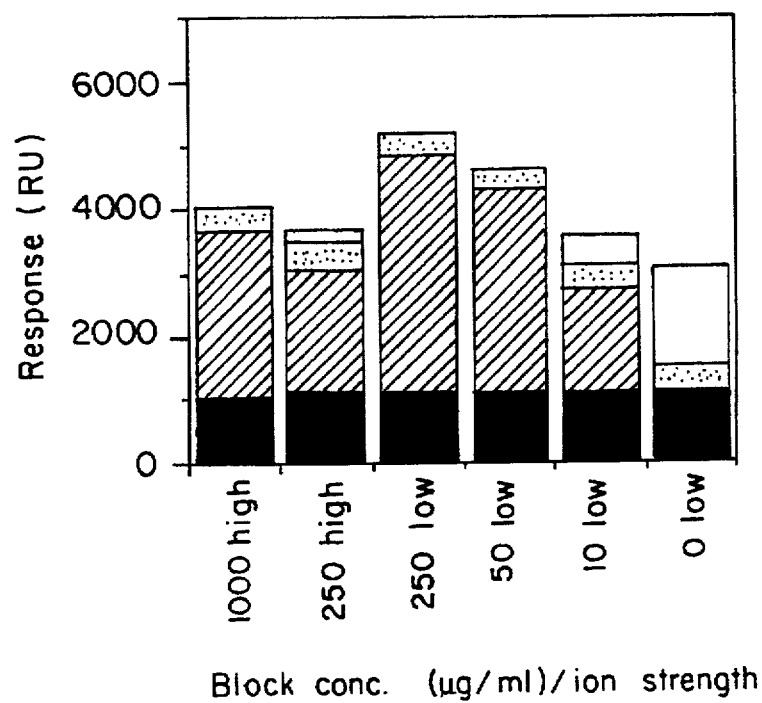
FIG. 8 is a similar staple diagram as in FIGS. 5 to 7 but with purified monoclonal and with higher concentration of monoclonal added in the second addition than in the first addition thereof.
Figure 9:
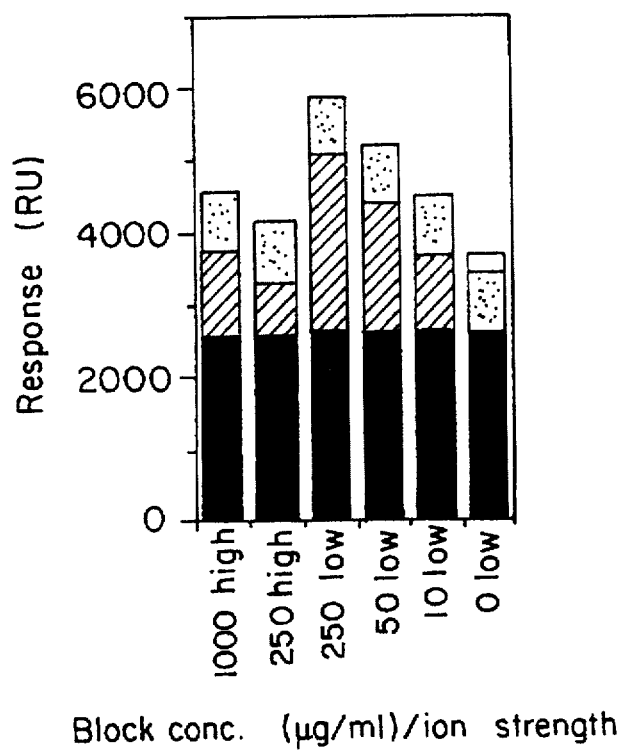
FIG. 9 is a similar staple diagram as in FIG. 8 with purified monoclonal but with the same concentration thereof used for both the first and the second addition of the monoclonal.

FIG. 8 illustrates the responses when using purified monoclonal 10 at 7 µg/ml as the first monoclonal and at 70 µg/ml as the second monoclonal, whereas FIG. 9 shows the responses when the concentration of purified monoclonal 10 is 70 µg/ml in both cases.

Figure 10:
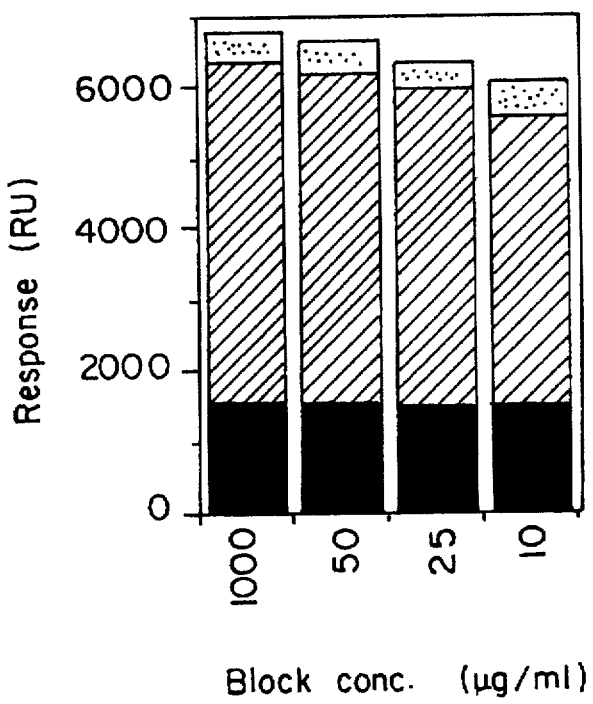
FIG. 10 is a similar staple diagram as in FIGS. 5 to 9 for the response at low ionic strength for four different blocking antibody concentrations.

In FIG. 10 it is shown that as low blocking antibody concentrations as 25 µg/ml function efficiently at low ionic strength; at 10 µg/ml a small response was obtained when injecting the second monoclonal.

The present invention is, of course, not restricted to the above specifically described embodiments, but many variations and modifications are within the scope of the general inventive concept as stated in the following claims.

We claim:

1. An assay method, comprising the step of binding a second substance to a first substance immobilized on a solid phase surface modified by a charged matrix, said first substance being either a ligand or a species bound directly or indirectly thereto, said first substance specifically binds with said second substance, wherein said solid phase surface having said first substance immobilized thereto exhibits a residual electric charge, and wherein the reaction for binding said second substance to said first substance is performed at an ionic strength below 100 mM, and at such pH conditions that the electric charge of said second substance is opposite to that of said solid phase surface so that said second substance is electrostatically attracted by said solid phase surface, to be concentrated thereto, and then determining the amount of said second substance bound to said first immobilized substance.

2. The method according to claim 1, wherein the step of binding said second substance is followed by a step of subjecting said surface to ionic strength conditions of at least 150 mM.

3. The method according to claim 1 wherein said second substance is selected from the group consisting of proteins, modified proteins, polypeptides, and fragments thereof.

4. The method according to claim 3, wherein said second substance is an antibody or a fragment thereof.

5. The method according to claim 1, wherein the reaction for binding said second substance to said first substance is an immunochemical reaction.

6. The method according to claim 1, wherein said ionic strength is below 20 mM.

7. The method according to claim 1, wherein said second substance is a secondary reagent in a sandwich assay for binding to an analyte which has first bound to a ligand immobilized to said surface.

8. The method according to claim 7, wherein said second substance is an antibody.

9. The method according to claim 1, wherein said solid phase surface comprises an electrically charged hydrogel surface layer.

10. The method according to claim 1, wherein said solid phase surface is a sensing surface for surface plasmon resonance based measurements.

11. The method according to claim 1, wherein said second substance is a secondary reagent in an ELISA assay for binding to an analyte which has first bound to a ligand immobilized to said surface.

12. The method according to claim 1, wherein said ligand or species bound directly or indirectly thereto is an analyte or a secondary reagent bound to said analyte.

13. The method according to claim 1, wherein said second substance is an analyte.

14. The method according to claim 1, wherein said first substance is selected from the group consisting of a protein, a polypeptide, a protein fragment, a polypeptide fragment, a hapten, a hormone, a sugar, biotin, a toxin, and a vitamin.

15. The method according to claim 14, wherein said protein or polypeptide is selected from the group consisting of an antigen, an antibody, protein A, protein G, an enzyme, a lectin, and avidin.

16. The method according to claim 1, wherein said solid phase surface comprises a dextran layer bound to a metal surface.

17. The method according to claim 1, wherein said ionic strength is below 50 mM.

18. The method according to claim 1, wherein said assay method is a solid phase immunochemical assay.

19. An assay method, comprising the steps of:
   (a) immobilizing a first substance on a solid phase surface modified by a charged matrix, said first substance being either a ligand or a species bound directly or indirectly thereto, wherein said solid phase surface having said first substance immobilized thereto exhibits a residual electric charge;
   (b) contacting said solid phase surface having said first substance immobilized thereto with a sample suspected of containing an analyte, wherein said analyte binds to said first immobilized substance;
   (c) contacting said solid phase surface with a second substance which binds to said analyte, wherein the reaction for binding said second substance to said analyte is performed at an ionic strength below 100 mM, and at such pH conditions that the electric charge of said second substance is opposite to that of said solid phase surface so that said second substance is electrostatically attracted by said solid phase surface; and
   (d) determining the amount of said second substance bound to said analyte.

20. The method according to claim 19, wherein the step of binding said second substance is followed by a step of subjecting said surface to ionic strength conditions of at least 150 mM.

21. The method according to claim 19, wherein said second substance is selected from the group consisting of proteins, modified proteins, polypeptides, and fragments thereof.

22. The method according to claim 19, wherein said second substance is an antibody or a fragment thereof.

23. The method according to claim 19, wherein the reaction for binding said second substance to said first substance is an immunochemical reaction.

24. The method according to claim 19, wherein said ionic strength is below 20 mM.

25. The method according to claim 19, wherein said solid phase surface comprises an electrically charged hydrogel surface layer.

26. The method according to claim 19, wherein said solid phase surface is a sensing surface for surface plasmon resonance based measurements.

27. The method according to claim 19, wherein said solid phase surface comprises a dextran layer bound to a metal surface.

28. The method according to claim 19, wherein said ionic strength is below 50 mM.

29. The method according to claim 19, wherein said assay method is a solid phase immunochemical assay.

30. An assay method, comprising the step of binding a first substance to binding sites on a solid phase surface modified by a charged matrix,
   said first substance being either a ligand or a species bound directly or indirectly thereto,
   wherein said solid phase surface having said first substance immobilized thereto exhibits a residual electric charge,
   contacting said solid phase surface having said first substance immobilized thereto with a second substance,
   said second substance being a substance that blocks residual binding sites on said solid phase surface after immobilization of said first substance thereto, and
   wherein the reaction for binding said second substance to said residual binding sites is performed at an ionic strength below 100 mM, and at such pH conditions that the electric charge of said second substance is opposite to that of said solid phase surface so that said second substance is electrostatically attracted by said solid phase surface;
   contacting said solid phase surface with a sample suspected of containing an analyte, wherein said analyte binds to said first immobilized substance; and
   determining the amount of said analyte bound on said solid phase surface.

31. The method according to claim 30, wherein the step of binding said second substance is followed by a step of subjecting said surface to ionic strength conditions of at least 150 mM.

32. The method according to claim 30, wherein said second substance is selected from the group consisting of proteins, modified proteins, polypeptides, and fragments thereof.

33. The method according to claim 30, wherein said second substance is a non-specific antibody or a fragment thereof.

34. The method according to claim 30, wherein the reaction for binding said analyte to said first substance is an immunochemical reaction.

35. The method according to claim 30, wherein said ionic strength is below 20 mM.

36. The method according to claim 30, wherein said solid phase surface comprises an electrically charged hydrogel surface layer.

37. The method according to claim 30, wherein said solid phase surface is a sensing surface for surface plasmon resonance based measurements.

38. The method according to claim 30, wherein said solid phase surface comprises a dextran layer bound to a metal surface.

39. The method according to claim 30, wherein said ionic strength is below 50 mM.

40. The method according to claim 30, wherein said assay method is a solid phase immunochemical assay.

* * * * *